US007623246B2

United States Patent
Ho et al.

(10) Patent No.: US 7,623,246 B2
(45) Date of Patent: Nov. 24, 2009

(54) OPTICAL SENSING DEVICES WITH SPR SENSORS BASED ON DIFFERENTIAL PHASE INTERROGATION AND MEASURING METHOD USING THE SAME

(75) Inventors: Ho Pui Ho, Kowloon (CN); Chi Lok Wong, Fanling (CN); Shu Yuen Wu, Wah Fu (CN); Wing Cheung Law, Kwai Chung (CN); Chinlon Lin, Shatin (CN); Siu Kai Kong, Kowloon (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 12/046,359

(22) Filed: Mar. 11, 2008

(65) Prior Publication Data

US 2008/0304072 A1 Dec. 11, 2008

Related U.S. Application Data

(62) Division of application No. 11/178,077, filed on Jul. 8, 2005, now Pat. No. 7,365,855.

(51) Int. Cl.
*G01B 11/02* (2006.01)
*G01N 21/00* (2006.01)

(52) U.S. Cl. .................................. 356/492; 422/82.05

(58) Field of Classification Search ................. 356/481, 356/491, 492, 495, 517; 422/82.05, 82.08
See application file for complete search history.

(56) References Cited

U.S. PATENT DOCUMENTS

| 5,255,075 | A | 10/1993 | Cush et al. |
| 5,627,666 | A | 5/1997 | Sharp et al. |
| 6,628,376 | B1 | 9/2003 | Nikitin et al. |
| 6,907,254 | B1 | 6/2005 | Westfield |
| 6,934,068 | B2 * | 8/2005 | Kochergin .................. 359/280 |
| 7,027,676 | B2 * | 4/2006 | VanWiggeren et al. ........ 385/14 |
| 7,292,349 | B2 * | 11/2007 | Miller et al. ................. 356/504 |

(Continued)

FOREIGN PATENT DOCUMENTS

CN    1237705    12/1999

(Continued)

OTHER PUBLICATIONS

Great Britain Search Report dated Apr. 21, 2005 for Great Britain Patent Application No. GB0427374.4.

(Continued)

*Primary Examiner*—Patrick J Connolly
(74) *Attorney, Agent, or Firm*—Darby & Darby PC

(57) ABSTRACT

Disclosed is an optical sensing device, which comprises a light source emitting a light; a beam splitter; an SPR sensor unit comprising a sensing surface; and a detecting mechanism; and a converting unit converting the first beam and the second beam from the optical device into a two-dimensional interference fringe pattern. From the above-mentioned configuration, an extra phase shift of a detection beam in SPR phase measurement is obtained. The differential measurement approach has shown to achieve a sensitivity figure significantly better than the best result that can be obtained from the prior art in the field of the measurement based on an SPR sensor.

20 Claims, 8 Drawing Sheets

U.S. PATENT DOCUMENTS

| | | | | |
|---|---|---|---|---|
| 7,339,681 | B2* | 3/2008 | Su et al. | 356/491 |
| 7,365,855 | B2* | 4/2008 | Ho et al. | 356/450 |
| 2002/0180979 | A1 | 12/2002 | Chou et al. | |
| 2003/0030817 | A1 | 2/2003 | Lee et al. | |
| 2003/0103208 | A1 | 6/2003 | Quinn et al. | |
| 2003/0128414 | A1 | 7/2003 | Watanabe et al. | |
| 2004/0004780 | A1 | 1/2004 | Watanabe | |
| 2004/0142482 | A1* | 7/2004 | Westphal et al. | 436/164 |
| 2005/0020240 | A1 | 1/2005 | Minter | |
| 2005/0194523 | A1* | 9/2005 | VanWiggeren et al. | 250/225 |
| 2005/0254542 | A1 | 11/2005 | Ahn et al. | |
| 2006/0046746 | A1 | 3/2006 | Ranford et al. | |
| 2007/0008546 | A1* | 1/2007 | Ho et al. | 356/481 |
| 2007/0037566 | A1 | 2/2007 | D'Agostino et al. | |
| 2007/0139646 | A1 | 6/2007 | Singh | |
| 2007/0139648 | A1 | 6/2007 | Singh | |
| 2007/0146718 | A1 | 6/2007 | Takase et al. | |
| 2007/0159629 | A1* | 7/2007 | Eing et al. | 356/369 |
| 2007/0166763 | A1* | 7/2007 | Ho et al. | 435/7.1 |
| 2008/0304072 | A1* | 12/2008 | Ho et al. | 356/450 |

FOREIGN PATENT DOCUMENTS

| | | |
|---|---|---|
| CN | 1342894 | 4/2002 |
| CN | 1393689 | 1/2003 |
| CN | 1588064 | 3/2005 |
| EP | 1130456 | 9/2001 |
| EP | 1328078 A2 | 7/2003 |
| EP | 1331745 A1 | 7/2003 |
| WO | 02/056506 A2 | 7/2002 |
| WO | 2005/076502 A1 | 8/2005 |
| WO | 2006/064240 A1 | 6/2006 |

OTHER PUBLICATIONS

Great Britain Search Report dated Mar. 22, 2006 for Great Britain Patent Application No. GB0525537.7.

Ho, H. P. et al., Real-time Optical Biosensor Based on Differential Phase Measurement of Surface Plasmon Resonance, Biosensors and Bioelectronics, Apr. 2005, 20:2177-2180.

Ho, H.P et al., "Surface Plasmon Resonance Sensor Based on the Measurement of Different Phase," Review of Scientific Instruments, Oct. 2002, 73(10):3534-3539.

Homola, J. et al., "Surface Plasmon Resonance Sensors: Review," Sensors and Actuators, 1999, B54:3-15.

International Search Report and Written Opinion mailed Apr. 26, 2007, which issue during the prosecution of International Patent Application No. PCT/CN2007/000182.

International Search Report and Written Opinion mailed Jun. 5, 2008, which issued during the prosecution of International Patent Application No. PCT/US08/54605.

International Search Report and Written Opinion mailed May 30, 2005 for International Patent Application No. PCT/GB2005/000362.

International Search Report mailed Mar. 9, 2006 for International Patent Application No. PCT/GB2005/004842.

Kabashin, A. V. et al, "Surface Plasmon Resonance Interferometer For Bio- And Chemical-sensors," Optics Communications, May 1998, 150:5-8.

Liedberg, Bo et al., "Surface Plasmon Resonance for Gas Detection and Biosensing," Sensors and Actuators, 1983, 4:299-304.

Nelson, S. G. et al., "High Sensitivity Surface Plasmon Resonance Sensor Based on Phase Detection," Sensors and Actuators, Sep. 1996, B35-36:187-191.

Nikitin, P. I. et al., "Surface Plasmon Resonance Rnterferometry for Micro-array Biosensing," Sensors and Actuators, 2000, 85:189-193.

Preliminary Amendment to U.S. Appl. No. 10/597,465 mailed Apr. 27, 2007 (16 pages).

Preliminary Amendment to U.S. Appl. No. 11/721,966, which was mailed Jan. 22, 2008 (13 pages).

Shen, Shuai et al., "Optical Phase-shift Detection of Surface Plasmon Resonance," Applied Optics, Apr. 1998, 37:(10)1747-1751.

Sheridan, Anna K. et al., "Phase Interrogation of an Integrated Optical SPR Sensor," Sensors and Actuators, Jan. 2004, B97:114-121.

Slavik, Radan et al., "Miniaturization of Fiber Optic Surface Plasmon Resonance Sensor," Sensors and Actuatorsm, 1998, B51:311-315.

U.S. Appl. No. 10/597,465 mailed Jul. 26, 2006 (8 pages).

U.S. Appl. No. 11/721,966 mailed Jun. 15, 2007 (8 pages).

Wu, Chien-Ming et al., "High-sensitivity Sensor Based on Surface Plasmon Resonance and Heterodyne Interferometry," Sensors and Actuators, Jul. 2003, B92:133-136.

Wu, S. Y. et al., "Highly Sensitive Differential Phase-sensitive Surface Plasmon Resonance Biosensor Based on the Mach-Zehnder Configuration," Optics Letters, Oct. 2004, 29(20): 2378-2380.

* cited by examiner (a)

(b)

OPTICAL SENSING DEVICES WITH SPR SENSORS BASED ON DIFFERENTIAL PHASE INTERROGATION AND MEASURING METHOD USING THE SAME

CROSS-REFERENCE TO RELATED APPLICATIONS

This patent application is a Divisional of U.S. patent application Ser. No. 11/178,077 filed on Jul. 8, 2005, to which priority is claimed, and the entire contents of which are hereby incorporated by reference.

TECHNICAL FIELD OF THE INVENTION

This invention relates to surface plasmon resonance (SPR) sensors, and particularly to optical surface plasmon resonance sensors based on differential phase interrogation and phase enhancement using a Fabry-Perot cavity for detection of a molecular species.

BACKGROUND OF THE INVENTION

Various types of optical sensors utilizing SPR measurement have been reported since the first gas detection and biosensing sensor based on SPR was developed by Nylander et al., "Surface plasmon Resonance for gas detection and biosensing" by Lieberg, Nylander and Lundstrom in Sensors and Actuators, Vol. 4, page 299. Traditional sensing technique for extracting information from SPR is primarily concerned with analyzing angular and wavelength properties of a reflected light beam within the resonant reflectance dip.

Nelson et al. presented the first SPR sensing based on optical phase detection (Sensors and Actuators B, 35-36, 187-191, 1996). The phase quantity has a steep slope response and therefore offers the potential for at least 3 times greater resolution than sensors based on conventional angle and wavelength modulation.

However, Nelson's phase detection system is very sensitive to mechanical vibrations and phase errors incurred in the system may become problematic. System stability issues of Nelson's system limit its applications. Phase detection improvements under "noisy" environment have been widely studied.

Recent research's attention to the SPR sensing has shifted to measuring the SPR phase shift, because the resonant phase behavior exhibits a steep jump, which leads to the potential in achieving extremely high sensitivity.

The most recent work was presented by Chien-Ming Wu et al., who reported a heterodyne interferometric system for the investigation of phase variation during surface plasmon resonance (Sensors and Actuators B 92, 133-136, 2003). The system used a combined SPR with total internal reflection (TIR) so that an extra phase shift caused by TIR may be added to a detected signal. In addition, a reference optical path is employed in the system to suppress unwanted noise. But the drawback is that the sensor response is measured by monitoring the phase shift versus incident angle, which requires highly stable mechanical parts. Also, the reference optical path is not totally identical to the signal path. Therefore, common-mode noise may still exist in the differential measurement.

Sheridan analyzed the phase behavior of an SPR waveguide sensor (Sensors and Actuators B 97, 114-121, 2004). The system employed a Mach-Zehnder interferometer (MZI) configuration with two sensing branches. Since only one branch was exposed to index variation, unwanted refractive index changes common to two branches such as temperature variation are said to be suppressed. This device was found to provide a higher sensitivity than the conventional single-waveguide configuration.

FIG. 6 shows a conventional sensing device with an SPR sensor of the Kretschmann configuration, of which the detailed description and discussion can be found in the articles by H. P. Ho, et al., "Real-time optical biosensor based on differential phase measurement of surface plasmon resonance" (BIOSENSORS & BIOELECTRONICS, 20 2177-2180, 2005), and by S. Y. Wu, et-al., "Highly sensitive differential phase-sensitive surface plasmon resonance biosensor based on the Mach-Zehnder configuration" (OPTICS LETTERS 29, 2378-2380, 2004). Their entire disclosure is incorporated herein by reference.

As shown in FIG. 6, a light beam from an He-Ne laser source 1' is divided into two beams Is and Ir by a 50:50 beam splitter 2'. In a signal path, the beam Is enters a silver sensing surface 41' of a sensing head 4', while the beam Ir is reflected by a mirror surface 3' in a reference path. The two beams are recombined at a beam splitter 5' and form interference pattern. After passing through a Wollaston prism 6', SPR images are captured by a detection device 7', and then are input to a data processor 8' for analysis.

Although the differential SPR phase approach as shown in FIG. 6 has improved measurement accuracy significantly, similar to other SPR phase techniques, the problem existing in the SPR phase approach is that the distribution of SPR phases over the sensing surface is not recorded. The information obtained from the mapping of surface reactions which can be directly inferred from the SPR phase distribution is necessary and important for many bio-reaction monitoring applications. For example, users may want to perform bio-sensing of a range of analytes from a single sample simultaneously. The capability of the SPR phase imaging is particularly important. In addition, given that the phase imaging imposes more stringent requirements on an optical instrument due to a relatively low signal to noise ratio and a low frame rate (i.e. low data collection speed) achievable by a common imaging device such as CCDs, it is necessary to further develop the current differential SPR phase technique, in order to provide a better signal to noise ratio for the imaging measurement, while enabling the phase to be stepped as required at a speed appropriate to the imaging device.

SUMMARY OF THE INVENTION

In general, the present disclosure describes an optical sensing device having a sensing surface, which can enhance the phase shift of an incident beam caused by the SPR effect, for example, by permitting the incident beam to pass through the sensing surface at least twice.

In exemplary embodiments, the present disclosure describes methods of detecting biological, biochemical, or chemical characteristics of a species.

To achieve the objects aforementioned, according to one aspect of the present invention, there is provided an optical sensing device comprising:

a light source emitting a light;

a beam splitter configured to divide the light into a first beam and a second beam, wherein the beam splitter allows the first beam to pass therethrough while reflecting the second beam;

an SPR sensor unit comprising a sensing surface, wherein the first beam from the splitter is reflected by the sensing surface at least twice and be sent back to the splitter; and a detecting mechanism comprising:

a reflecting unit reflecting the second beam from the beam splitter and the first beam coming from the sensor unit through the beam splitter, and a converting unit converting the first beam and the second beam from the reflecting unit into a two-dimensional interference fringe pattern.

According to an embodiment of the invention, the optical sensing device of the invention further comprises a data processor for analyzing interference patterns detected by the detecting mechanism.

According to embodiments of the invention, the sensor unit comprises a 60° equilateral SF18 glass prism which is coated with a metal layer. A sensitive material may be placed on the metal layer directly or through an intermediate material. The sensitive material can be an antibody that binds complementarily a corresponding antigen. A flow channel made from chemically inert Teflon may be attached to the surface of the sensitive material. It should be noted that any chemically and biological inert material in addition to Teflon can also be used for the flow cell.

According to another aspect of the invention, there is provided a method of detecting biological, biochemical, or chemical characteristics of a species, comprising: providing a device comprising an SPR sensor having a sensing surface;

allowing a fluid including the species through a channel attached to the sensing surface;

subjecting a light to passing through the SPR sensor so that the light is reflected at least twice by the sensing surface;

obtaining a two-dimensional interference fringe pattern of the light from the SPR sensor;

measuring a differential phase between a p-polarization and an s-polarization of the light through analyzing the two-dimensional interference fringe pattern; and determining the biological, biochemical, or chemical characteristics of the species in accordance with the differential phase.

According to one embodiment of the method, the step of measuring the differential phase comprises:

averaging an interference fringe pattern of the light over a region to produce a profile of an intensity variation for each of the p- and s-polarization interference fringe patterns;

extracting an intensity distribution of each of the p- and s-polarization interference fringe patterns from the profile to obtain a curve of the intensity distribution of each of the p- and s-polarization interference fringe patterns;

differentiating the curve to find a peak of each of the curves; and obtaining the differential phase through a location of the peak of each of the curves.

According to still another aspect of the invention, there is provided an optical sensing device, comprising:

a light source emitting a light;

a beam splitter configured to divide the light into a first beam and a second beam, wherein the beam splitter allows the first beam to pass therethrough while reflecting the second beam;

an SPR sensor unit magnifying a phase change of the first beam from the beam splitter; and a detecting mechanism comprising:

a reflecting unit reflecting the second beam from the beam splitter and the first beam coming from the SPR sensor unit through the beam splitter, and a converting unit converting the first beam and the second beam from the reflecting unit into a two-dimensional interference fringe pattern.

DETAILED DESCRIPTION OF THE INVENTION

The present invention and various advantages thereof will be described with reference to exemplary embodiments in conjunction with the drawings.

One aspect of the invention provides an optical sensing device, comprising: a light source emitting a light; a beam splitter configured to divide the light into a first beam and a second beam, wherein the beam splitter allows the first beam to pass therethrough while reflecting the second beam; an SPR sensor unit magnifying a phase change of the first beam from the beam splitter; and a detecting mechanism comprising a reflecting unit reflecting the second beam from the beam splitter and the first beam coming from the SPR sensor unit through the beam splitter, and a converting unit converting the first beam and the second beam from the reflecting unit into a two-dimensional interference fringe pattern.

Figure 1:
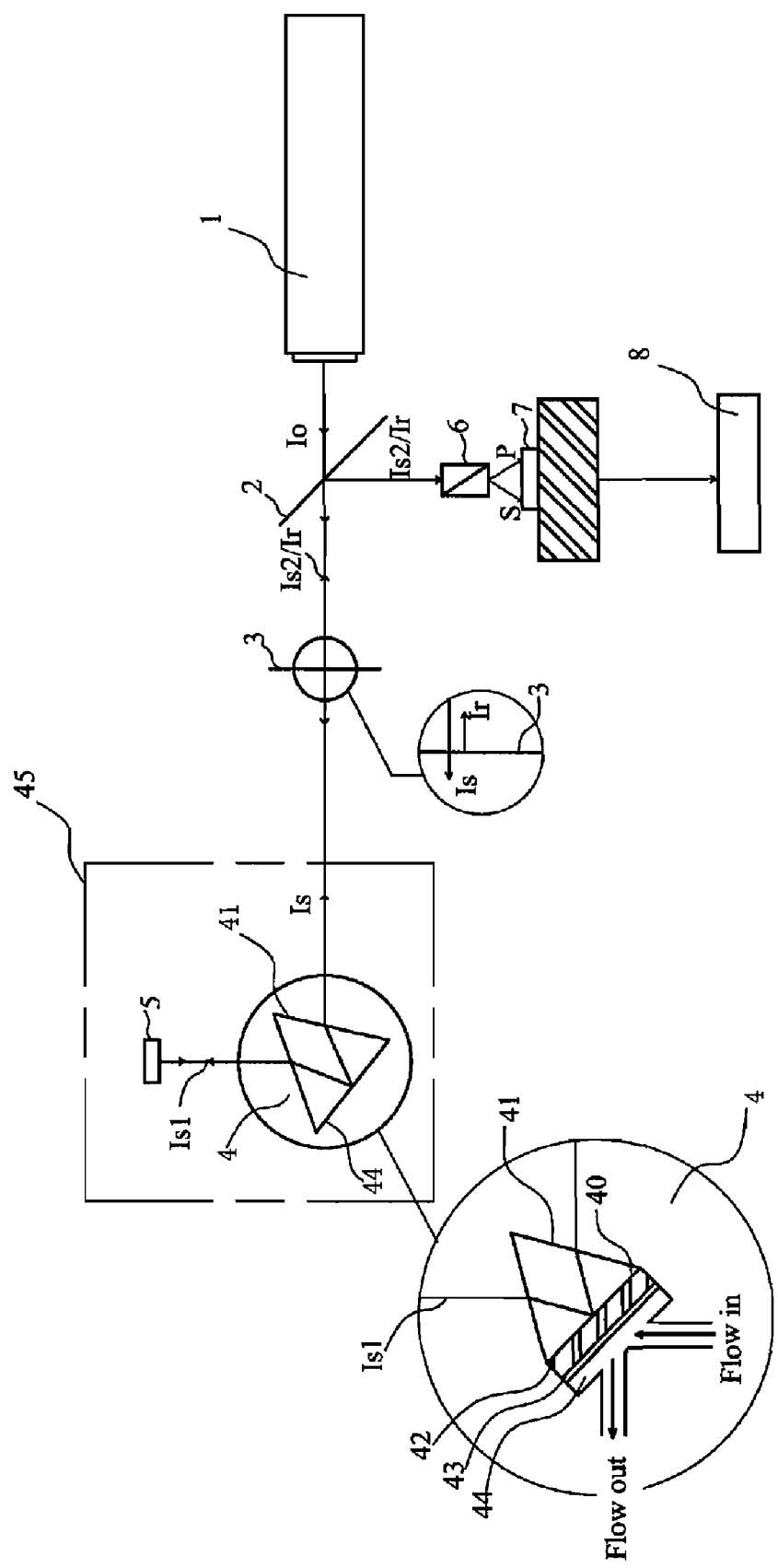
FIG. 1 is a schematic diagram of an optical sensing device with an SPR sensor of this invention.

An optical sensing device according to one embodiment of the present invention is shown in FIG. 1. The device comprises an excitation light source 1 such as a random polarization He—Ne laser source, which emits a beam I0. An optical device 2 is provided in a path of the beam I0 from the light source 1, and disposed at an angle of 45° with respect to the path. An SPR sensor unit 45 is provided downstream in the path to receive the beam I0. A beam splitter 3 is provided between the optical device 2 and the unit 45.

The beam splitter 3 separates the beam IO passing through the optical device 2 into two beams Is and Ir, the beam Is passing through the splitter 3, while the beam Ir being reflected back to the optical device 2.

The SPR sensor unit 45 comprises a sensing surface 40 which is disposed in a manner that the beam from the splitter 3 can be reflected by itself at least twice. According to an embodiment of the invention, as shown in FIG. 1, the SPR sensor unit 45 comprises an SPR sensor 4 and a reflecting mirror 5.

In one preferred embodiment, the SPR sensor is a 60° equilateral SF18 glass prism 41, which is disposed as shown in FIG. 1. In this embodiment, the mirror 5 is disposed to reflect the beam reflected by the sensing surface 40 back to it.

Then the beam reflected by the mirror is reflected by the sensing surface 40 back to the splitter 3. In such a manner, the beam passing through the splitter 3 is reflected twice by the sensing surface and sent back to the splitter.

In this embodiment, the 60° equilateral SF18 glass prism 41 is coated with a metal layer 42. A sensitive material 43 is further placed on the surface of the metal layer 42. The metal layer 42 can be formed by first sputtering a silver layer of about 48 nm on the glass prism 41 to provide a sensing surface 40 and then sputtering a gold layer of about 3 nm (not shown) on the silver layer to be a protective layer for the sensing surface of the silver layer. The sensitive material 43 can be an antibody that binds complementarily a corresponding antigen. In addition, a channel 44 made from e.g. chemically inert Teflon is attached to the surface of the sensitive material 43.

The light beam I0 from the light source 1 first passes through the optical device 2 without attenuation and then is divided into two beams by the beam splitter 3: one is the penetrated beam Is to be used as a detecting light and the other beam is the reflected beam Ir to be used as a reference light. Then, the beam Is enters the SPR sensor 4. At a resonance incident angle, the beam Is enters the sensing surface 40 first time to form a beam Is1 which experiences a first phase shift caused by surface plasmon resonance effect. Then the beam Is1 is reflected by the sensing surface 40. By providing the mirror 5 at the end of the optical cavity, the beam Is1 is reflected and enters the sensing surface 40 again (second time) at the same incident angle. An extra phase shift is thereby added to the beam Is1. Then the beam Is1 passes through the beam splitter 3 again (as beam Is2). Finally, the penetrated beam Is2 recombines with the reference beam Ir to form a required interference signal.

It should be noted that, although in the above embodiment, the phase variance of the beam Is1 caused by SPR effect is enhanced by using the mirror 5 to bounce back the beam Is1 reflected from the sensing surface, other manners for enhancing the phase variance are readily conceivable to those skilled in the art.

A Wollaston prism 6 for separating a polarized optical interference signal beam into a p-polarization component and an s-polarization component is placed in front of a digital two-dimensional array detector 7 such as a CCD camera to receive the combined beam from the optical device 2. Since only a p-polarization light is affected by the SPR effect, and an s-polarization light is served as a reference signal, the above optical system can be considered as two independent interferometers operating in parallel. The advantage of this configuration is that any unwanted common mode phase drift caused by mechanical, temperature or other kind of variations can be eliminated through measurement of the differential phase between p- and s-polarization signals. Finally, two interference fringes pattern related to both the polarizations are captured by the digital CCD camera.

The captured patterns are input into a data processor 8 to be analyzed by a fringes analysis process, for which a program written by e.g. Math Lab can be used. An embodiment of the fringes analysis process will be described hereinafter with reference to FIG. 3.

Figure 2:
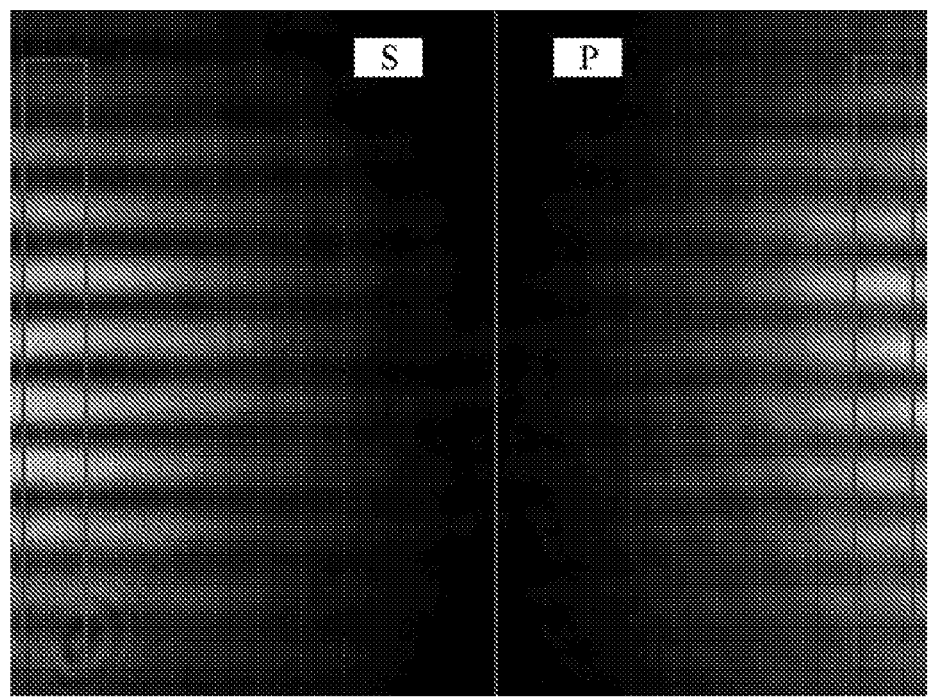
FIG. 2a is an SPR sensor interference fringe pattern image obtained in an air detection.
FIG. 2b is a graph showing corresponding intensity distributions of the s- and p-polarized beam.
Figure 2:
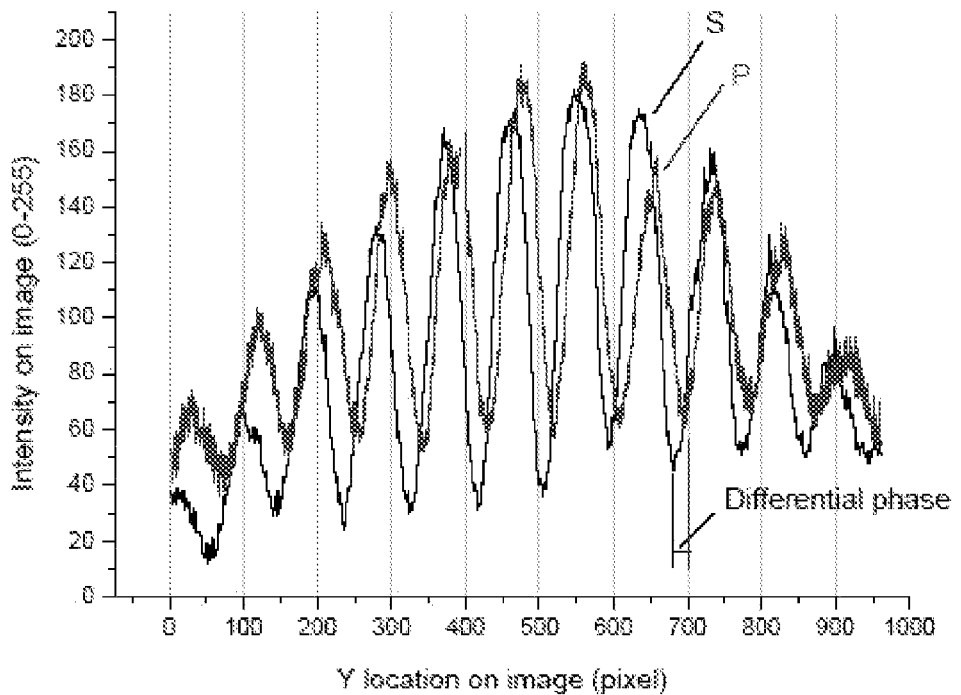
Figure 3:
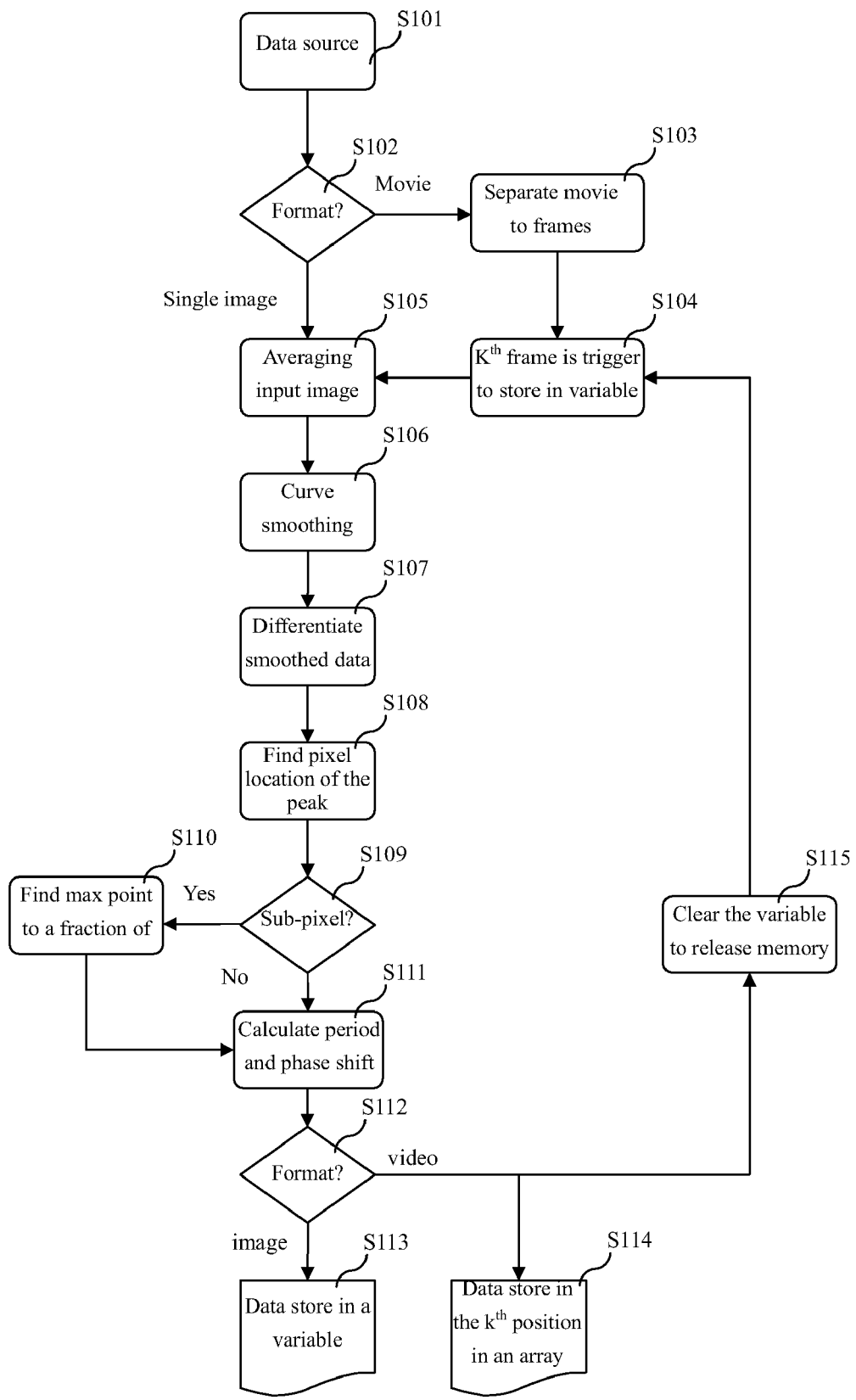
FIG. 3 is a block diagram for illustrating the fringe analysis method according to the invention.

Referring to FIG. 3 now, in this process, the interference patterns are read from a data source (S101) and the data format thereof is identified (S102). If the interference patterns are in a video format, then they are separated into frames (S103). The frames are triggered to be stored in variable (S104) and then are averaged (S105). On the other hand, if the interference patterns are a set of single images, they will also be averaged (S105). The averaging process involves first reading intensity values of pixels in a pre-defined rectangular region within an image. The rectangular region is then separated into one-pixel wide vertical traces each containing a different intensity value. These traces are separately averaged by finding a mean horizontal pixel value of each of all the vertical traces. Then a profile of the intensity variation of an interference signal is produced by the mean horizontal pixel values for the image. Effectively a two-dimensional interference pattern has finally been reduced to a one-dimensional array representing the averaging of the pattern. As shown in FIG. 2(*a*), for example, the two regions enclosed by the boxes have been averaged to produce two traces of interference signal. These traces will later be used for calculating a differential phase between the two orthogonal polarizations. The averaging operation is used to increase the stability of the intensity distribution curve extracted from the image. This provides a more accurate phase measurement. Then, the intensity distribution for each of the p- and s-polarization interference fringe patterns is extracted for each frame of images.

FIG. 2*b* is an intensity distributions plot for air sensing. A Fast Fourier Transform (FFT) followed by a low pass filtering is conducted for smoothing the curve of the intensity distribution (S106), which will results in a more accurate differential phase information.

The smoothed intensity distribution curve is differentiated (S107). Then, a peak in the distribution curve as represented in a pixel location is found by differentiating the curve (S108). In addition, a standard deviation of differential phase measurement between two frames can also be used to indicate a system measurement error. Then, whether or not the location of the peak is an integer pixel value is determined (S109).

If the location of the peak is an integer pixel value, the differential phase between the p- and s-polarization intensity distribution curves is obtained by comparing the location of the peak of the two sinusoidal waveforms represented in the pixel location (S111). If it is not an integer pixel value, the peak will be located as a fraction of pixel (sub-pixel) by means of linear extrapolation using the intensity values of two adjacent pixels (110). Thus, the differential phase is obtained accordingly (S111).

Then, the differential phase value is stored according to the data format of the interference patterns (S112). If the interference patterns are in single image format, the differential phase value will be stored (S113). If the interference patterns are in video format, then the calculated differential phase will be stored in the kth position in a data array (S114). Then, the interference pattern of the next frame will go through step (S104) to step (S114). Finally the data array of differential phase values is obtained.

EXAMPLE 1

Figure 4:
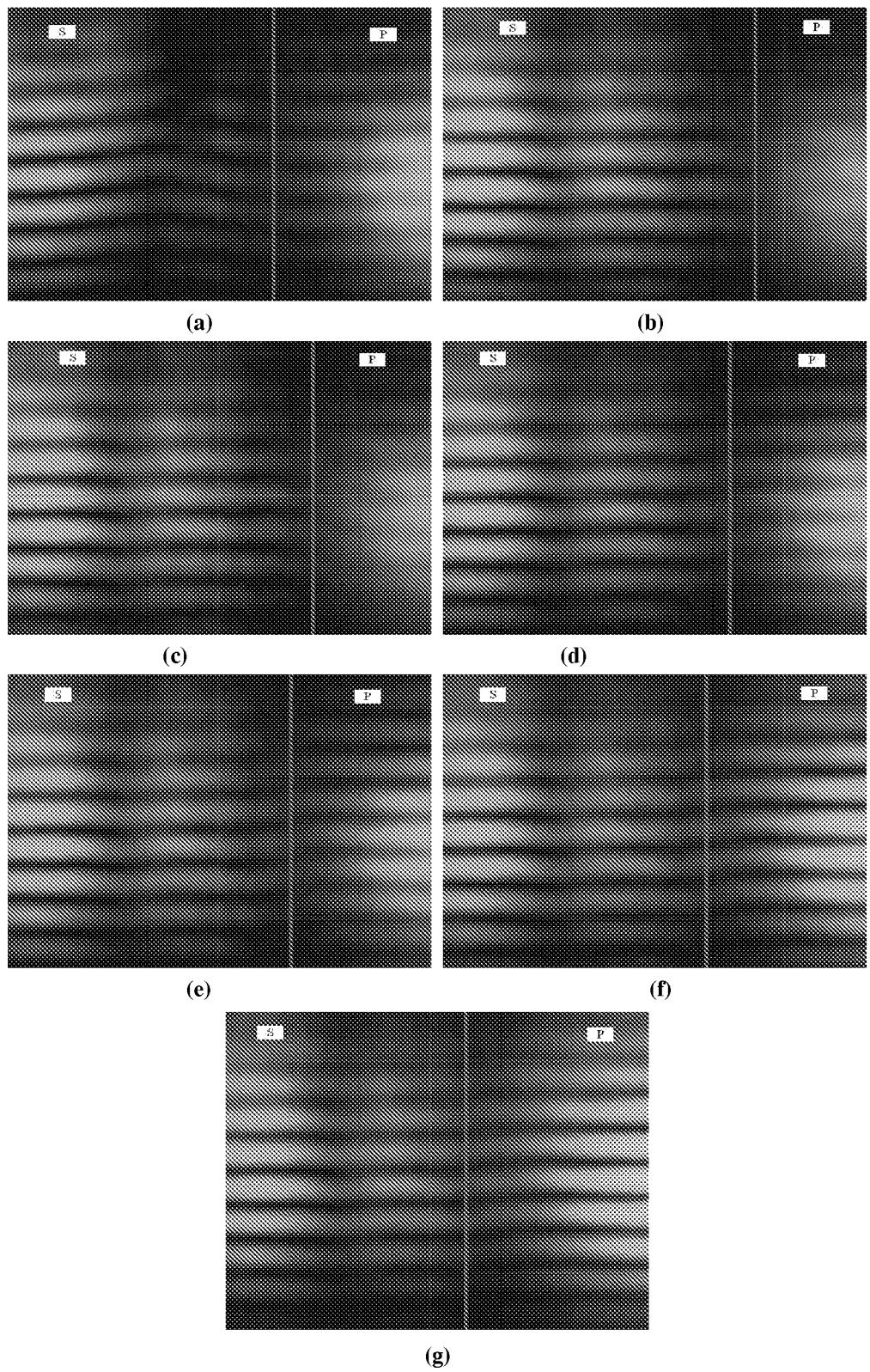
FIG. 4 shows the SPR fringe patterns of salt-water mixtures with various salt concentrations.

To demonstrate the performance of the present invention, salt-water sensing experiments were carried out using the device as shown in FIG. 1. A group of salt-water mixture samples were used. The concentrations of the samples were 0 wt %, 0.5 wt %, 1 wt %, 2 wt %, 3 wt %, 5 wt %, and 7 wt % respectively with the corresponding refractive index ranging from 1.3333 to 1.3453. A series of interference fringe pattern images obtained from the samples were recorded and shown in FIG. 4.

Figure 5:
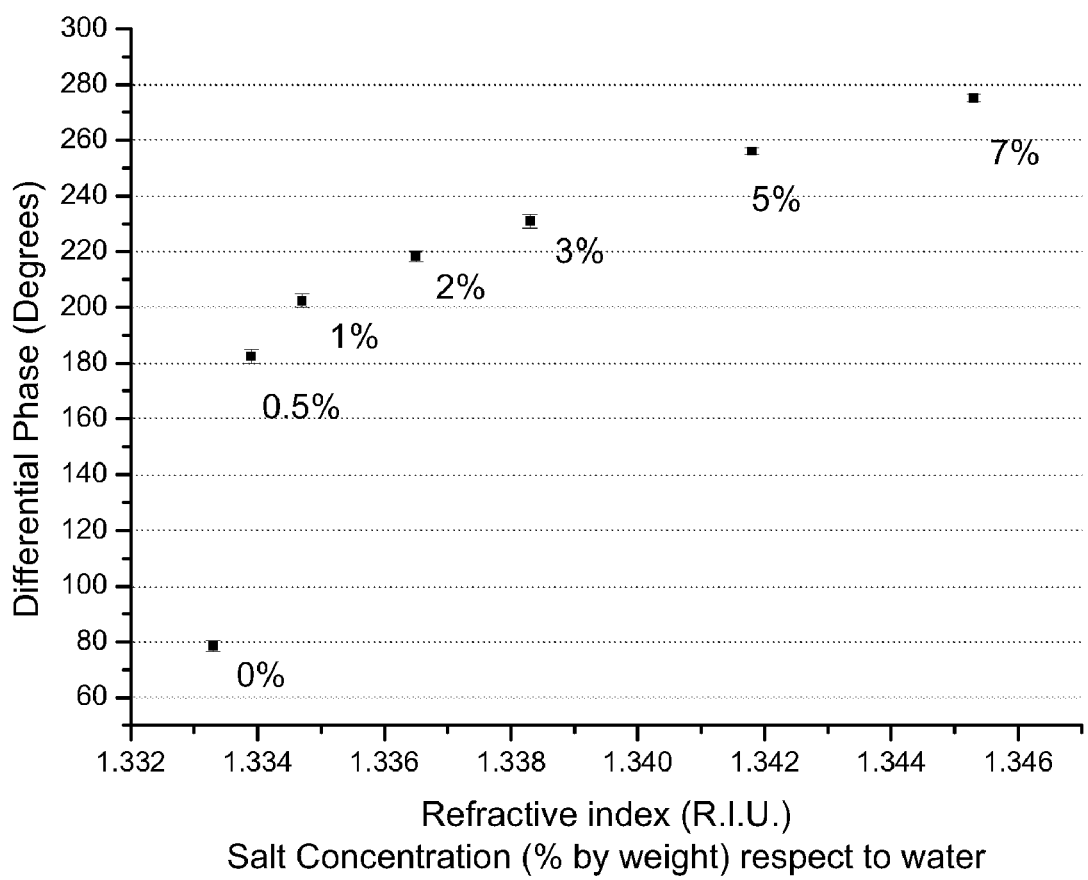
FIG. 5 is a graph showing the quantitative differential phase with respect to refractive index, which is obtained from the sensing device of the invention.

After processed by the fringe analysis method as mentioned above, quantitative differential phase values were obtained and plotted in FIG. 5. The phase response was found to be $6.1 \times 10^{-5}$ RI/degree with an uncertainty of $1.7 \times 10^{-2}$ rad. The calculated system sensitivity was $1.2 \times 10^{-4}$ RIU.

Figure 6:
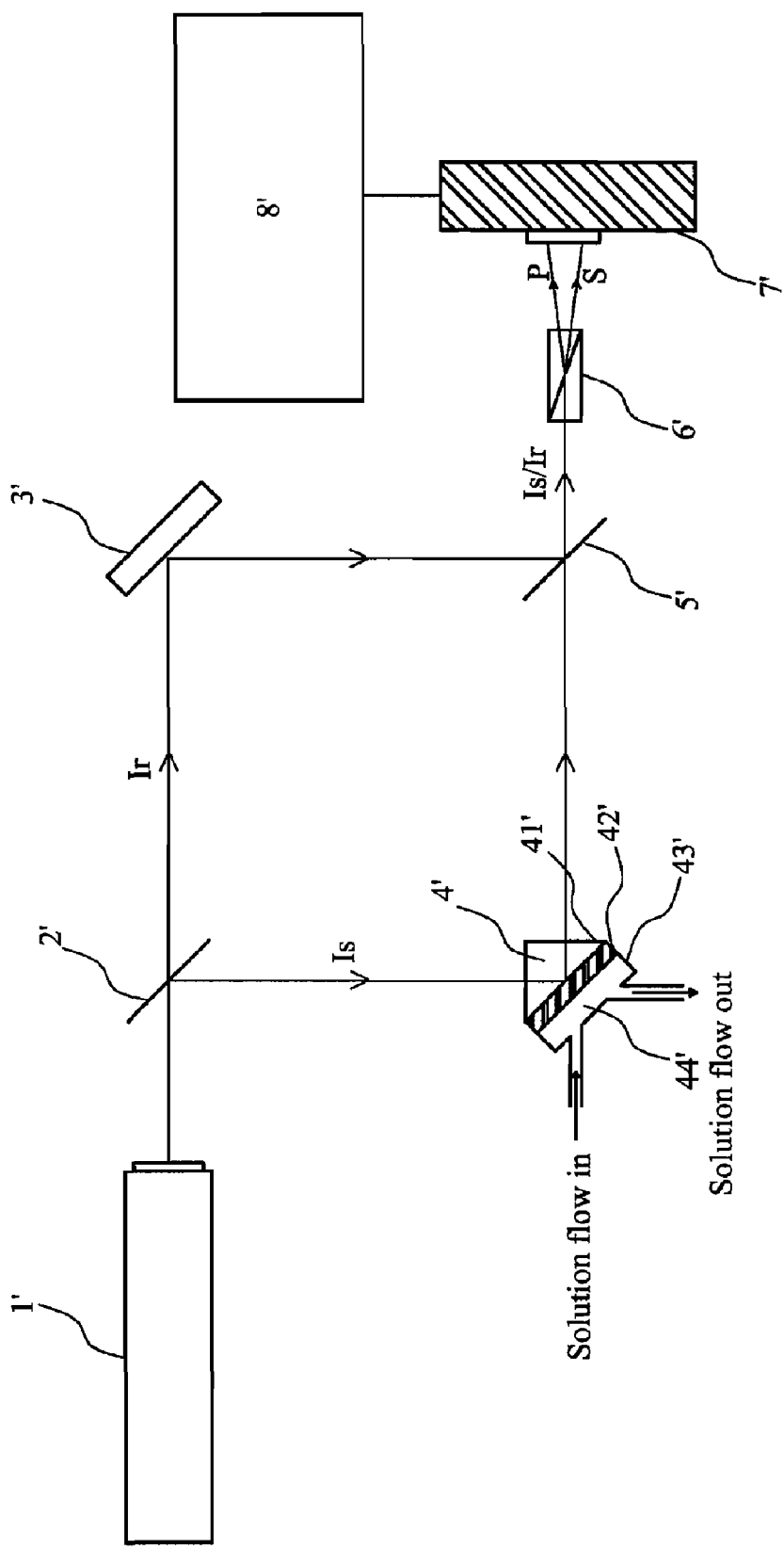
FIG. 6 is a diagram showing the schematic layout of a conventional sensing device based on a Mach-Zehnder interferometer (MZI)
Figure 7:
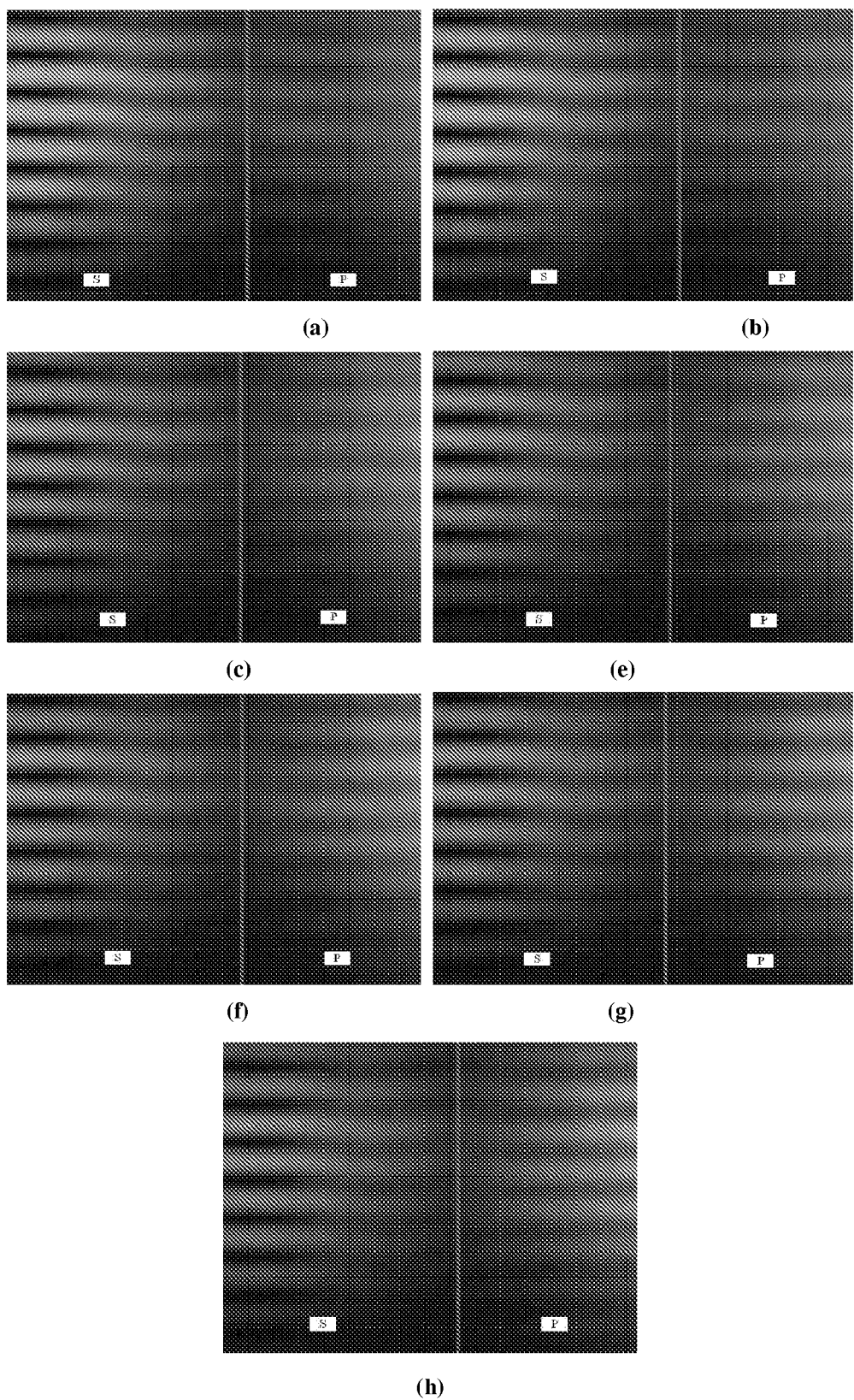
FIG. 7 shows the SPR fringe patterns of salt-water mixtures of various salt concentration obtained by conventional sensing device as shown in FIG. 6.
Figure 8:
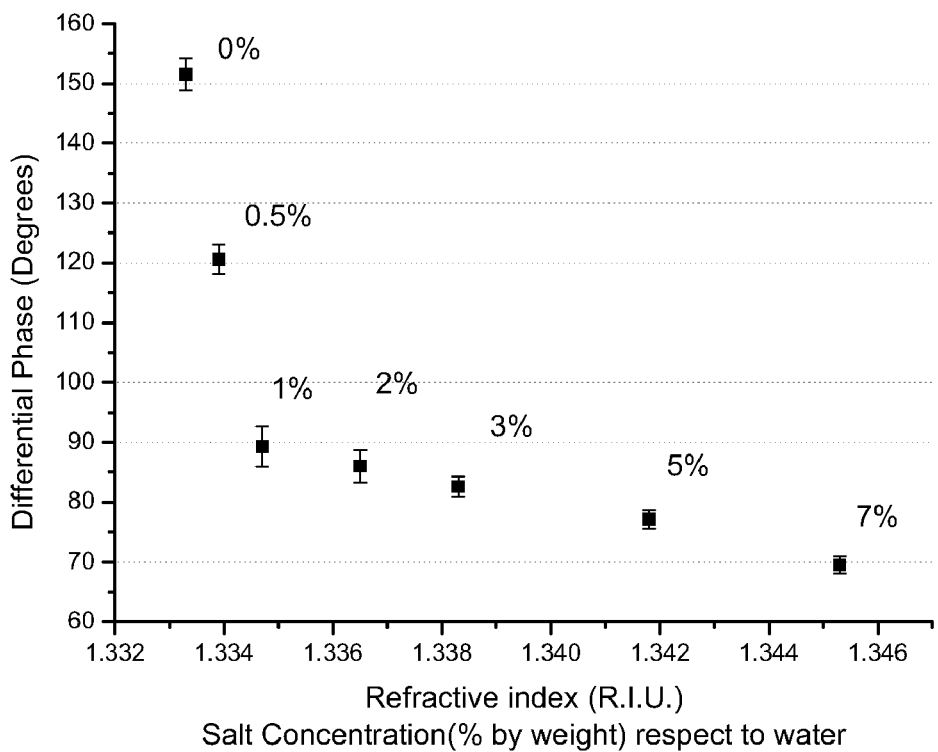
FIG. 8 is a graph showing the quantitative differential phase obtained from a conventional sensing device as shown in FIG. 6 with respect to refractive index.

In order to show the phase measurement enhancement by the present invention, a conventional SPR phase detection set-up based on the Mach-Zehnder interferometer as shown in FIG. 6 was used to repeat the measurement of the salt-water mixture samples. As explained previously, in this conventional configuration, the light beam only entered the sensing surface once and no extra phase shift was present. Measurement was conducted for salt-water mixture samples with concentrations being 0 wt %, 0.5 wt %, 1 wt %, 2 wt %, 3 wt %, 5 wt %, and 7 wt % respectively by using the same analysis method. The interference fringes pattern images were shown in FIGS. 7a-7h. Corresponding differential phase values were plotted against refractive index values in FIG. 8 and were further compared with previous results in FIG. 9.

Figure 9:
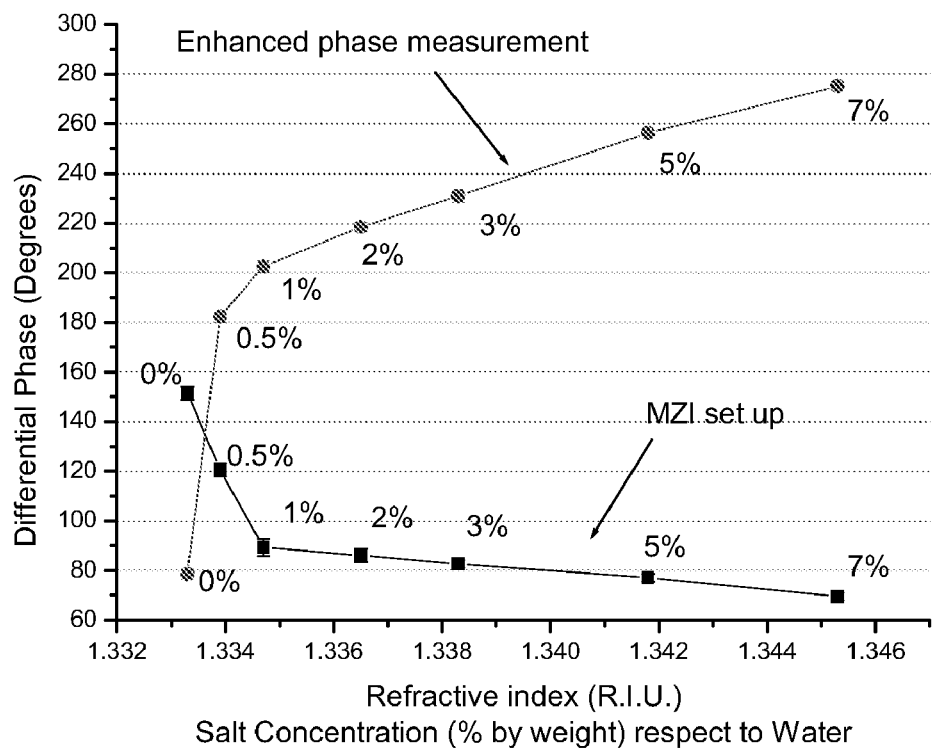
FIG. 9 is a graph showing the phase response enhancement resulted from the invention.

It can be seen from FIG. 9 that the rate of change of the differential phase shift for the phase enhanced SPR sensor according to the present invention is much steeper than that for the conventional SPR device. Particularly, the experimental results obtained from the salt-water mixture samples indicate that the phase response for the conventional device is about 1.5×10-4 RI/degree, compared with that for the phase enhanced SPR sensor of the invention, namely, 6.1. In other words, the present invention has enhanced the sensitivity by 2.8 times. This is a significant improvement over previously obtained results when gold is used as the sensor surface. Such an improvement in the sensitivity limit should allow SPR biosensors to become a possible replacement for conventional biosensing techniques based on fluorescence.

In conclusion, the present invention has many advantages. First, it offers higher sensitivity by increasing the phase shift. Second, the stability of phase measurement is enhanced because of differential measurement by using a Wollaston prism. Third, the invention offers 2-D mapping surface reactions in real time, which may find wide application in chemical, biochemical and biological processes. Fourth, the system is simple and can be manufactured at low cost.

While we have hereinbefore described embodiments of this invention, it is understood that our basic constructions can be altered to provide other embodiments which utilize the processes and compositions of this invention. Consequently, it will be appreciated that the scope of this invention is to be defined by the claims appended hereto rather than by the specific embodiments which have been presented hereinbefore by way of examples.

What is claimed as new and desired to be protected by Letters Patent is:

1. A method of detecting differential phase from a SPR sensor, comprising:
   receiving light reflected off an SPR sensor, wherein the light is reflected at least twice by the sensing surface;
   obtaining a two-dimensional interference fringe pattern image data of the received light using an image capture device; and
   measuring a differential phase between a p-polarization and an s-polarization of the light through analyzing the two-dimensional interference fringe pattern image data using a data processor.

2. The method of claim 1, wherein the measuring of a differential phase comprises:
   averaging an interference fringe pattern of the light to produce a profile of an intensity variation for each of a p-polarization and an s-polarization interference fringe patterns;
   extracting an intensity distribution of each of the p-polarization interference fringe pattern and the s-polarization interference fringe pattern respectively from the profile of the intensity variation to obtain a curve of the intensity distribution of each of the p-polarization and s-polarization interference fringe patterns;
   differentiating the curves respectively to find a peak of each of the curves; and
   obtaining the differential phase through a location of the peak of each of the curves.

3. The method of claim 2, wherein the averaging of an interference fringe pattern comprises:
   reading a value of a pixel over a pre-defined rectangular region within the pattern;
   separating the rectangular region into one-pixel wide vertical traces, each containing a different intensity value;
   finding a mean horizontal pixel value of each of all the vertical traces; and
   producing the profile of the intensity variation from the mean horizontal pixel values.

4. The method of claim 2, wherein the obtaining the differential phase comprises:
   comparing a location of the peak of each of the two curves, if the location is an integer pixel value; or
   locating the peak as a fraction of pixel by means of linear extrapolation using the intensity value of two adjacent pixels, if a location of the peak is not an integer pixel value, and comparing the location of the peak of each of the two curves.

5. The method of claim 1, wherein the light reflected at least twice from the SPR sensor is obtained by:
   receiving initially reflected light; and
   directing the initially reflected light back to the SPR sensor.

6. The method of claim 5, wherein the initially reflected light is directed back to the SPR sensor with a mirror.

7. The method of claim 1, further comprising:
   generating light for application to the SPR sensor;
   splitting the light into a first beam and a second beam using a beam splitter.

8. The method of claim 7, wherein the first beam reflects off the SPR sensor and the second beam reflects back from the beam splitter for use in obtaining the interference fringe pattern.

9. The method of claim 1, further comprising determining biological, biochemical, or chemical characteristics of a sample based at least in part on the analysis of the two-dimensional interference fringe pattern image data, wherein light has passed through the sample before being received using the image capture device.

10. The method of claim 1, wherein the p-polarization and s-polarization are separated by passing the received light through a Wollaston prism.

11. The method of claim 10, where the s-polarization pattern serves as a reference.

12. A method of detecting SPR sensor differential phase, comprising:
   splitting a beam of light into a first beam and a second beam;
   reflecting the second beam to an optical device;
   reflecting the first beam off an SPR sensor a first time and a second time and to the optical device;
   separating a p-polarization component and an s-polarization component of both the reflected first beam and the reflected second beam;
   obtaining a two-dimensional interference fringe pattern of the separated reflected first beam and separated reflected second beam for both the p-polarization component and the s-polarization component;
   capturing the interference fringe patterns with an image capture device;

measuring the differential phase between the interference fringe pattern for the p-polarization component and the s-polarization component using a data processor.

13. The method of claim 12, wherein measuring the differential phase comprises:

averaging the interference fringe pattern to produce a profile of an intensity variation for each of a p-polarization and a s-polarization interference fringe patterns;

extracting an intensity distribution of each of the p-polarization interference fringe pattern and the s-polarization interference fringe pattern respectively from the profile of the intensity variation to obtain curves of the intensity distribution of each of the p-polarization and s- polarization interference fringe patterns;

differentiating the curves respectively to find at least one peak of each of the curves; and obtaining the differential phase through a location of the at least one peak of each of the curves.

14. The method of claim 13, wherein the averaging of an interference fringe pattern comprises:

reading a value of a plurality of pixels over a pre-defined rectangular region within the pattern;

separating the rectangular region into one-pixel wide vertical traces, each containing a different intensity value;

finding a mean horizontal pixel value of each of all the vertical traces; and producing the profile of the intensity variation from the mean horizontal pixel values.

15. The method of claim 13, wherein measuring the differential phase comprises:

comparing a location of the at least one peak of each of the p-polarization and s-polarization intensity distribution curves.

16. The method of claim 13, wherein the obtaining the differential phase comprises:

locating the at least one peak as a fraction of a pixel by means of linear extrapolation.

17. The method of claim 12, wherein the optical device:

separates the beam for polarization into p-polarization and s-polarization;

forms the interference fringe pattern; and captures the interference fringe pattern.

18. The method of claim 17, wherein p-polarization and s-polarization are separated by passing the received light through a Wollaston prism.

19. The method of claim 18, where the s-polarization pattern serves as a reference.

20. The method of claim 12, further comprising determining biological, biochemical, or chemical characteristics of a sample based at least in part on the analysis of the interference fringe patterns, wherein light has passed through the sample before being received using the image capture device.

* * * * *